(12) United States Patent
Ooi et al.

(10) Patent No.: US 7,312,818 B2
(45) Date of Patent: Dec. 25, 2007

(54) IRIS IMAGE PICKUP APPARATUS

(75) Inventors: Koji Ooi, Yokohama (JP); Ken Ikoma, Yokohama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 661 days.

(21) Appl. No.: 10/201,452

(22) Filed: Jul. 23, 2002

(65) Prior Publication Data

US 2003/0020828 A1    Jan. 30, 2003

(30) Foreign Application Priority Data

Jul. 24, 2001   (JP)   ............... P. 2001-223218

(51) Int. Cl.
*H04N 5/225*   (2006.01)
(52) U.S. Cl. ............ 348/207.99; 348/78; 382/117
(58) Field of Classification Search ............ 348/78, 348/207.99; 382/117
See application file for complete search history.

(56) References Cited

U.S. PATENT DOCUMENTS 4,299,464 A * 11/1981 Cushman ............... 396/157
5,852,670 A * 12/1998 Setlak et al. ............ 382/126
6,064,752 A *  5/2000 Rozmus et al. .......... 382/117
6,320,610 B1 * 11/2001 Van Sant et al. ......... 348/143
6,591,001 B1 *  7/2003 Oda et al. ................ 382/117
6,856,695 B1 *  2/2005 Nakamura et al. ....... 382/124
2002/0131623 A1 *  9/2002 Musgrave et al. ....... 382/117

FOREIGN PATENT DOCUMENTS

JP         10-5195        1/1998

\* cited by examiner

*Primary Examiner*—Tuan Ho
*Assistant Examiner*—Anthony J Daniels
(74) *Attorney, Agent, or Firm*—Pearne & Gordon LLP

(57) ABSTRACT

An optical axis of a telephotographic camera for picking up an enlarged image of an iris is placed between guide unit for guiding a subject K into a range in which an iris image can be picked up and direction indication guide unit for indicating the direction in which the subject K is to be directed. If the subject K wears glasses, the face direction of the subject K is changed as indicated by the direction indication guide unit so that an image of illumination light from an iris lighting fixture on the lens, etc., of the glasses of the subject K does not overlap the iris image.

20 Claims, 3 Drawing Sheets

IRIS IMAGE PICKUP APPARATUS

BACKGROUND OF THE INVENTION

This invention relates to an iris image pickup apparatus for picking up an iris image used for individual identification, etc., of a security system and in particular to an iris image pickup apparatus suited for efficiently picking up a good iris image that can be used for iris authentication processing.

If a subject wears glasses, illumination light glares on the picked-up image of the iris used for authentication processing and the percentage of the illumination light image overlapping the iris image is raised, lowering the authentication rate of the iris. Then, a conventional iris image pickup apparatus in a related art is designed for preventing such lowering the authentication rate of the iris.

For example, as described in Japanese Patent Publication No. H10-5195, when illumination light for picking up an iris image is applied to an eyeball, whether the iris image is good or NG is determined based on the amount of illumination reflected light (when the subject wears glasses, the reflected light amount is much) and if the iris image is determined a bad image (the reflected light amount is much and the illumination light glares on the glasses), illumination is applied to the eyeball from another incidence angle and again an image of the eyeball is picked up as the illumination light is applied, and whether the image is good or NG is determined in a similar manner. After this, the procedure of applying the illumination light to the eyeball at various incidence angles and determining whether the iris image is good or NG is repeated until a good image is provided (an image with less reflected light amount is provided).

In the conventional iris image pickup apparatus described above, the illumination incidence angle is changed one after another and picking up an image is repeated until a good iris image with no illumination light glaring on the iris part is provided, and thus it may take a long time until a good iris image is provided; this is a problem. To prevent the illumination light from glaring on the iris part, the interval from the camera to the lighting fixture must be taken wide; this is also a problem.

Further, with the conventional iris image pickup apparatus, when an image is picked up is not known and thus the probability that an iris image pickup failure will occur due to a blink of the subject is high, and there is a possibility that the whole time taken for authentication may be prolonged as the number of times an image is picked up is increased; this is a problem.

SUMMARY OF THE INVENTION

It is therefore an object of the invention to provide an iris image pickup apparatus that can efficiently provide a good iris image even if a subject wears glasses.

To the end, according to the invention, there is provided an iris image pickup apparatus comprising an image pickup unit for picking up an iris image of a subject and a direction indication guide unit for indicating a direction in which the subject is directed, wherein the image pickup unit and the direction indication guide unit are placed apart from each other with the optical axis of the image pickup unit toward the subject direction between.

In doing so, if the subject wears glasses and illumination light impinges on the lens, etc., of the glasses, the direction of the subject can be changed by the direction indication guide unit so that illumination reflection by the lens, etc., of the glasses is prevented from glaring on the iris part. Thus, the number of times a bad image is picked up is decreased and if the number of times an iris image is picked up is small, it is made possible to efficiently acquire a good image for iris authentication.

To the end, according to the invention, there is provided an iris image pickup apparatus comprising a first image pickup unit for picking up an image of a subject by a wide-angle lens, a second image pickup unit for picking up an iris image of the subject by a telephoto lens, and a direction indication guide unit, when it is determined that the subject wears glasses from image pickup information of the first image pickup unit, the direction indication guide unit for displaying guide indication for changing the direction of the subject's face before the second image pickup unit picks up an iris image.

Thus, whether or not the subject wears glasses is determined based on the picked-up image through the wide-angle lens and if the probability that the iris image will become bad is high, the direction of the subject is changed before an iris image is picked up so as not to provide a bad image, so that it is made possible to acquire a good iris image in the shortest time.

To the end, according to the invention, there is provided an iris image pickup apparatus comprising a first image pickup unit for picking up an image of a subject by a wide-angle lens, a second image pickup unit for picking up an iris image of the subject by a telephoto lens, a direction indication guide unit for indicating the direction in which the subject is directed, and an iris illumination unit for applying illumination light in an iris direction of the subject, wherein the first image pickup unit and the second image pickup unit are placed between the direction indication guide unit and the iris illumination unit and wherein a control unit, when it is determined that the subject wears glasses from image pickup information of the first image pickup unit, operates the direction indication guide unit for changing the direction of the subject before the second image pickup unit picks up an iris image.

Thus, the distance between the direction indication guide unit and the iris illumination unit is taken large, whereby if the probability that illumination light from the iris illumination unit will glare on the iris part is high, it is made possible to eliminate glaring the illumination light on the iris part simply by changing the direction of the subject's face only a little.

Further, the iris image pickup apparatus of the invention is characterized by the fact that the direction indication guide unit for indicating the direction in which the subject is directed is provided with a function of informing the subject of the iris image pickup timing. Accordingly, the subject can know the iris image pickup timing and can have consciousness of preventing a blink, and an iris image pickup failure caused by a blink and an increase in the processing time caused by again picking up an iris image can be prevented.

Further, the iris image pickup apparatus of the invention is characterized by the fact that the direction indication guide unit for indicating the direction in which the subject is directed is implemented as LEDs and the subject is informed of the iris image pickup timing according to the lighting pattern of the LEDs. Thus, the subject can be informed of the image pickup timing in an easy-to-understand manner.

Further, the iris image pickup apparatus of the invention is characterized by the fact that the subject is informed of the iris image pickup timing more than once. Accordingly, the chance that the subject has consciousness of preventing a blink is increased, and it is made possible to acquire an iris image in a state in which the subject relaxes.

Further, the iris image pickup apparatus of the invention is characterized by the fact that it comprises a flash unit for forcibly inducing the subject to blink. Accordingly, the subject can be made forcibly to blink before an iris image is picked up, an iris image can be picked up in a state in which the subject opens eyes after blinking, and an iris image pickup failure caused by a blink can be prevented.

Further, the iris image pickup apparatus of the invention is characterized by the fact that an iris image is also picked up before the subject is informed of the iris image pickup timing. Accordingly, an iris image can be picked up before the subject is informed of the image pickup timing, namely, before the subject is aware of the image pickup timing. If the iris image pickup results in success, then authentication can be started and it is made possible to speed up the whole processing. If a good iris image cannot be acquired, the subject is informed of the image pickup timing before an iris image is picked up. Thus, an iris image can be acquired reliably.

Further, the iris image pickup apparatus of the invention is characterized by the fact that it comprises a detection unit for detecting the distance to the subject, wherein the guide display position of the direction indication guide unit to indicate the direction in which the subject is directed is changed based on detection information provided by the detection unit, thereby controlling the direction in which the subject is directed. Accordingly, the inclination of the direction in which the subject should be directed can be optimized to avoid illumination reflection on glasses.

DETAILED DESCRIPTION OF THE PREFERRED EMBODIMENT

Referring now to the accompanying drawings, there is shown one embodiment of the invention.

Figure 1:
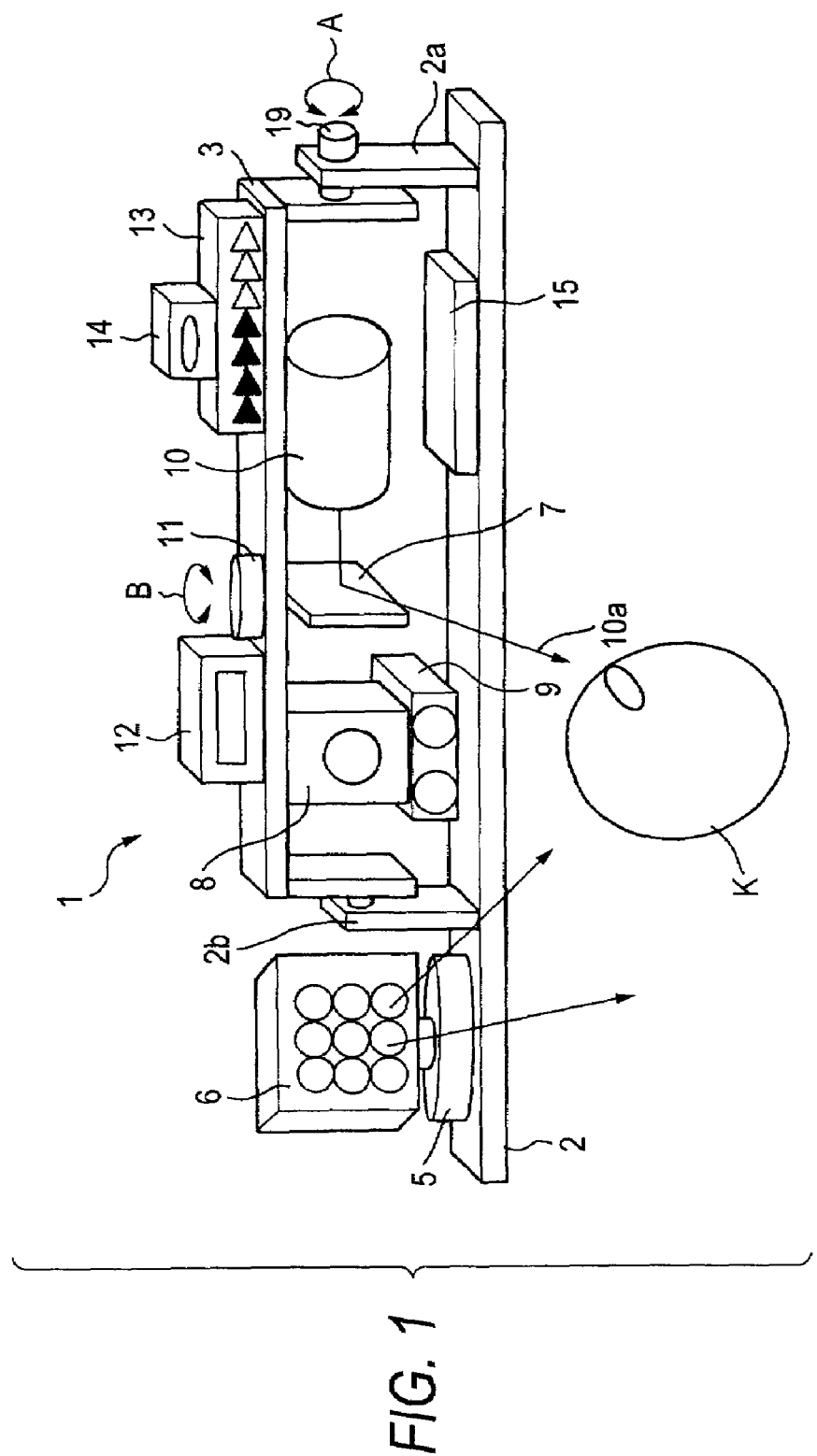
FIG. 1 is a drawing to show the configuration of an iris image pickup apparatus according to one embodiment of the invention.

FIG. 1 is a drawing to show the configuration of an iris image pickup apparatus 1 according to one embodiment of the invention. The iris image pickup apparatus 1 includes a base 2 and a tilt stand 3 supported between two support plates 2a and 2b placed upright on the base 2.

A pan motor 5 for iris lighting fixture is attached to the left end side of the base 2 and an iris lighting fixture 6 is attached to a rotation shaft of the pan motor 5 for iris lighting fixture. The iris lighting fixture 6 is directed in the iris direction by the pan motor 5 for iris lighting fixture and applies illumination light in the iris direction of a subject K. In the embodiment, the iris lighting fixture 6 is panned, but a motor for tilting the iris lighting fixture 6 can also be installed.

The tilt table 3 is supported for rotation in the arrow A direction by a tilt motor 19 attached to the support plate 2a.

A pan mirror 7 is installed substantially at the center of the inside of the tilt stand 3, a wide-angle camera 8 and a distance measurement sensor 9 are installed adjacent to the pan mirror 7 in the direction of the iris lighting fixture 6, and a telephotographic camera 10 is installed on the opposite side to the wide-angle camera 8 with the pan mirror 7 between.

The telephotographic camera 10 is put into a sideways position and an optical axis 10a of the telephotographic camera 10 is reflected on the pan mirror 7 and is directed substantially to the front of the iris image pickup apparatus 1. The pan mirror 7 can be rotated in the arrow B direction by a mirror pan motor 11 attached to the tilt table 3 and as the pan mirror 7 is rotated in the arrow B direction, the optical axis 10a of the telephotographic camera 10 is panned. As the tilt table 3 is rotated in the arrow A direction, the optical axis of the wide-angle camera 8 and the optical axis 10a of the telephotographic camera 10 are tilted.

On the outside of the tilt table 3, a guide unit 12 is installed at almost the same position as the wide-angle camera 8 and the optical axis 10a of the telephotographic camera 10. An indication guide unit 13 having a longitudinal structure is installed in the direction along the tilt table 3 on the opposite side to the guide unit 12 with the pan mirror 7 between, and a flash unit 14 for forcibly inducing the subject K to blink is installed on the direction indication guide unit 13.

The direction indication guide unit 13 is provided for indicating the direction in which the subject K is to be directed. The guide unit 12 and the direction indication guide unit 13 can also inform the subject K of the image pickup timing by the lighting method. The guide units 12 and 13 and the flash unit 14 are implemented as LEDs, but each may be any other display device such as an LCD.

As described above, in the embodiment, the guide unit 12 and the direction indication guide unit 13 are placed apart from each other with the optical axis 10a of the telephotographic camera 10 between and illumination light from the left iris lighting fixture 6 is applied to the subject K guided so as to see the front of the iris image pickup apparatus 1 as light is emitted by the guide unit 12 and when the iris image is determined bad and the direction indication guide unit 13 emits light, the subject K shakes his or her head in the direction crossing the optical axis 10a of the telephotographic camera 10 and sees the direction indication guide unit 13.

A controller 15 is placed on the base 2. The controller 15 controls the image pickup operation of the wide-angle camera 8 and the telephotographic camera 10 and also controls lighting the iris lighting fixture 6 and driving the pan motor 5 for: iris lighting fixture, the mirror pan motor 11, and the tilt motor 19 for tilting the tilt table 3. Further, the controller 15 controls lighting the guide unit 12, the direction indication guide unit 13, and the flash unit 14 as described later.

Next, the iris image acquisition procedure performed under the control of the controller 15 of the iris image pickup apparatus described above will be discussed according to a flowchart of FIG. 2.

The distance measurement sensor 9 of the iris image pickup apparatus 1 emits infrared light periodically. When reflected light of the infrared light is detected, the presence of a subject is known. First, at step S1, the subject is guided into a position where the subject views the guide unit 12 from the front in such a manner that the guide unit 12 is blink-displayed, etc., so that the subject enters the image pickup range of the front of the iris image pickup apparatus 1. At step S2, the distance to the subject is measured by the distance measurement sensor 9 and at step S3, a face image of the subject is picked up by the wide-angle camera 8. The distance information and the picked-up image provided here are used as information for controlling driving the pan motor 5 for iris lighting fixture, the mirror pan motor 11, and the tilt motor 19 to pick up an iris image later at step S7.

At step S4, whether or not the reflected light amount in the picked-up image by the wide-angle camera 8 is equal to or greater than a predetermined threshold value is determined. If the reflected light amount is equal to or greater than the predetermined threshold value, it is determined that the subject wears glasses, and control goes to step S5 and then to step S6. If it is not determined that the subject wears glasses, control goes to step S6 from step S4.

At step S5 to which control goes if the subject wears glasses, the direction indication guide unit 13 is blink-displayed, etc., for indicating the direction toward which the subject's face is to be directed. According to the indication, illumination reflection by the lenses of the glasses, etc., can be prevented from being put on the image of the iris part required for authentication.

Figure 3:
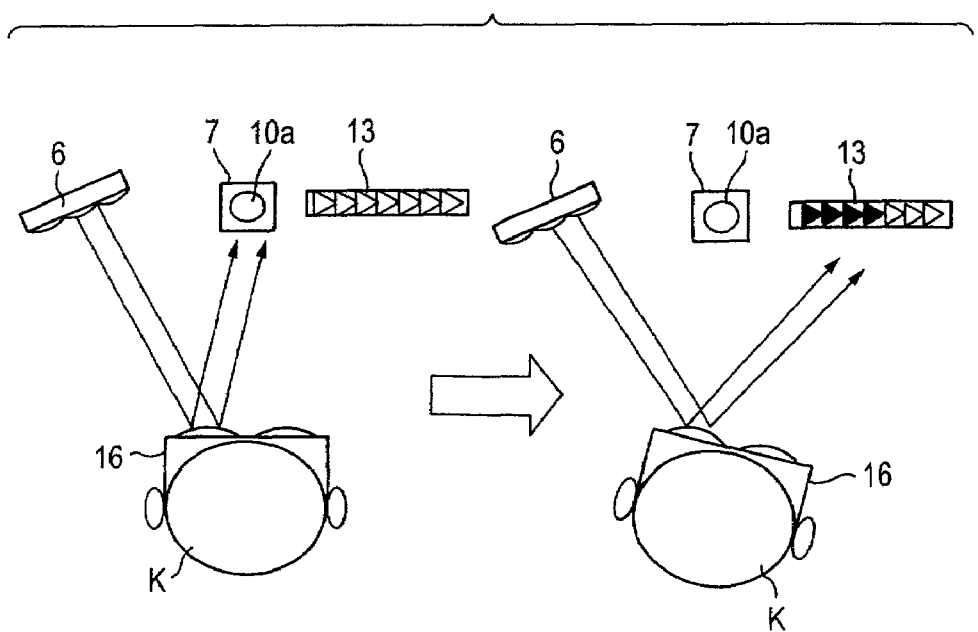
FIG. 3 is a schematic representation of a use method of direction indication guide unit in the embodiment of the invention.
Figure 4:
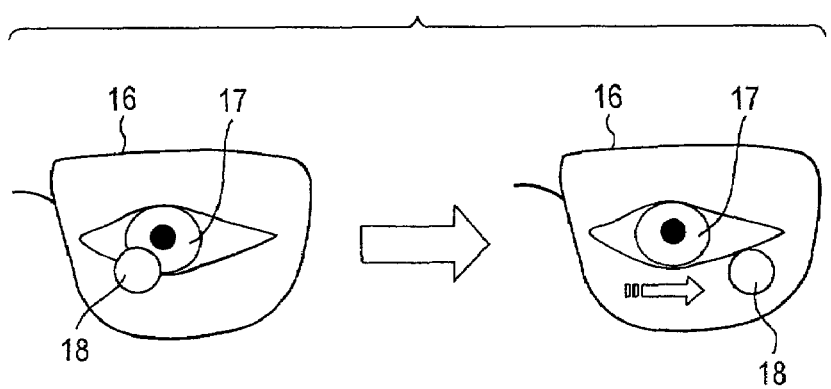
FIG. 4 is a schematic representation of preventing an illumination light image from glaring on an iris part in the embodiment of the invention.

For example, as shown at the left of FIG. 3, when illumination light from the iris lighting fixture 6 is applied to the iris of the subject K directed to the front by blink-displaying the guide unit 12 and an image of the iris is picked up by the telephotographic camera 10, if the subject K does not wear glasses, a good iris image can be acquired. However, if the subject K wears glasses 16, an illumination light image 18 glaring on the lens of the glasses 16 overlaps an iris image 17 of the subject, resulting in an iris image not suited for iris authentication, as shown at the left of FIG. 4.

Then, in the embodiment, if the subject K wears glasses, the face of the subject K is guided into the direction of the direction indication guide unit 13 by blink-displaying the direction indication guide unit 13, etc., as shown at the right of FIG. 3. Accordingly, the illumination light image 18 glaring on the lens of the glasses 16 is placed out of the iris image 17, as shown at the right of FIG. 4. If the subject K wears glasses, the direction of the face of the subject K is changed as shown at the right of FIG. 3 before control goes to step S6.

At step S6, the subject K is informed of the iris image pickup timing. For example, if the subject K does not wear glasses, the subject K is informed of the iris image pickup timing in such a manner that the blink period of the guide unit 12 is changed, that the lighting pattern is changed, or that the light color is changed. If the subject K wears glasses, the subject K is informed of the iris image pickup timing in such a manner that the blink period of the direction indication guide unit 13 is changed.

At step S7, an iris image is picked up. To pick up an iris image, the eyeball position is found by pattern matching, etc., from the face image picked by the wide-angle camera 8, the telephotographic camera 10 is focused on the eyeball using an automatic focusing technique, and an iris close-up image is picked up. At this time, the iris lighting fixture 6 is also directed to the iris direction and illumination light is applied to the iris.

At step S8, whether or not the iris image acquired at step S7 is an image suited for iris authentication (for example, whether or not the size of the iris in the image is within a predetermined range) is determined. If the iris image is an image suited for iris authentication, control goes to step S9, authentication processing. If the iris image is an image not suited for authentication processing, control returns to step S2 from step S8 and the steps of picking up a face image by the wide-angle camera 8 to picking up an iris image are again executed.

As described above, according to the iris image pickup apparatus of the embodiment, the direction indication guide unit 13 for indicating the direction in which the subject K is to be directed is placed at the predetermined position of the iris image pickup apparatus, whereby the illumination reflection image by the lens, etc., of the glasses that the subject K wears can be prevented from glaring on the iris part required for authentication and leading to picking up a bad image.

The guide unit 12 and the direction indication guide unit 13 are provided with the function of informing the subject K of the iris image pickup timing, whereby the subject K can take action of preventing a blink and the probability that an iris image pickup failure caused by a blink can be prevented is raised. Further, when picking up an iris image results in a failure, iris image pickup processing is again performed, namely, the subject K is informed of the iris image pickup timing more than once, so that the chance that the subject K can take action of preventing a blink is increased, and the subject K is given leeway.

Figure 2:
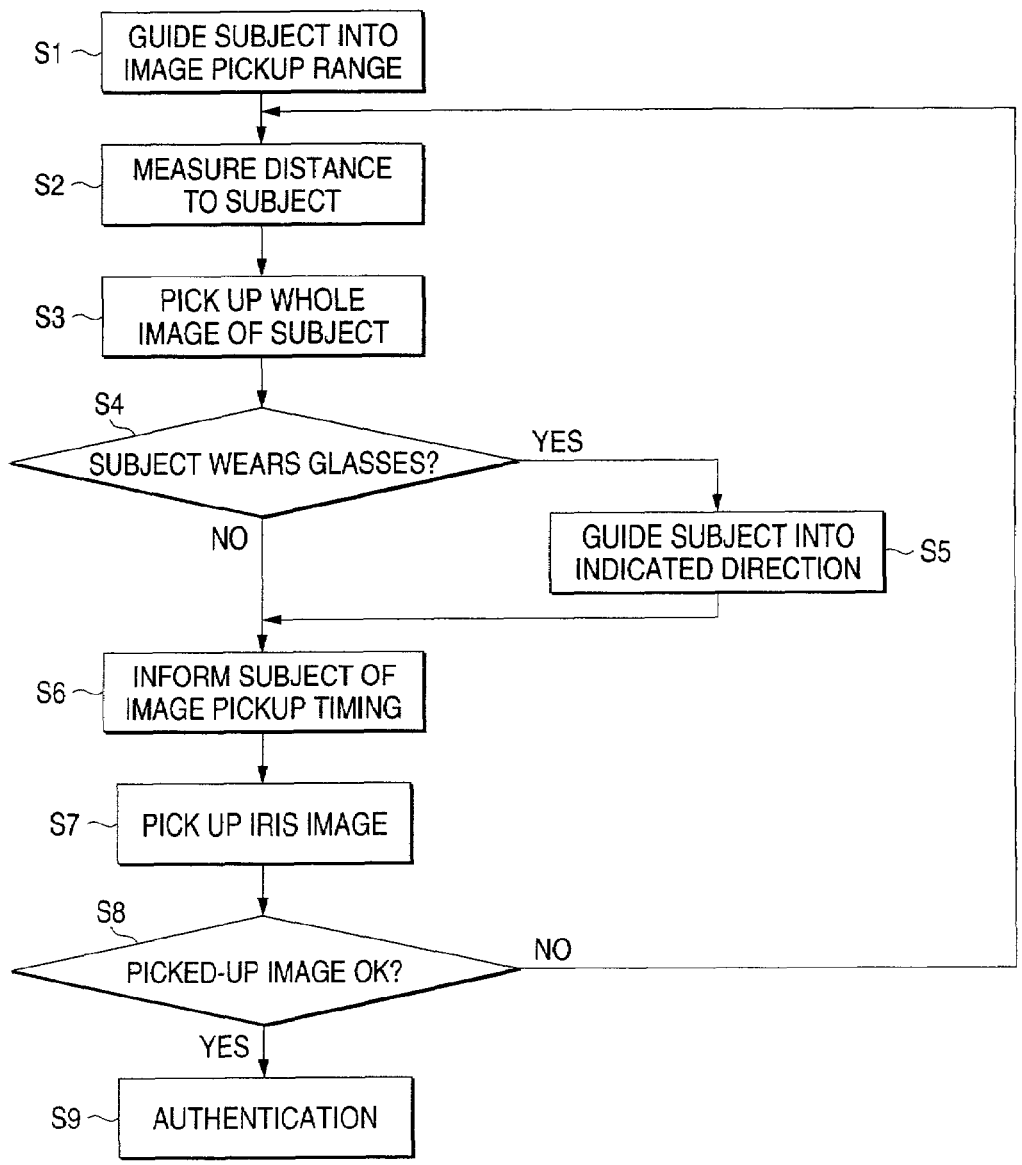
FIG. 2 is a flowchart to show an iris image acquisition procedure in the iris image pickup apparatus according to the embodiment of the invention.

An iris image can be acquired before step S6 in the flowchart of FIG. 2, that is, before informing the subject of the iris image pickup timing, and when the picked up iris image is no good, another iris image is acquired after informing the subject of the iris image pickup timing. If the iris image is acquired when the subject is not aware of it, the process can proceed to iris authentication processing and the whole process can be speeded up and if picking up the iris image results in a failure, when an iris image is again acquired, the subject is informed of the iris image pickup timing and thus it is made possible to acquire the iris image reliably.

The iris image pickup apparatus 1 according to the embodiment is provided with the flash unit 14. The flash unit 14 is snapped just before an iris image is picked up, whereby the subject K can be forcibly induced to blink and can be made to open the subject's eyes at the timing at which an iris image is picked up, and picking up an iris image can be prevented from failing. Thus, in the iris image pickup apparatus 1 according to the embodiment, the probability that an iris image will be again picked up due to a blink can be lessened and the processing time to iris authentication can be shortened.

The angle at which the effect of illumination reflection by the lens of the glasses can be circumvented varies depending on the illumination light incidence angle on the glasses of the subject K from their is lighting fixture 6. When the distance from the iris image pickup apparatus 1 to the subject K is short, if the inclination of the glasses is small, illumination refection can be prevented from glaring on the iris part when the distance is long, the inclination of the glasses needs to be increased. Then, in the iris image pickup apparatus 1 according to the embodiment, a plurality of LEDs, etc., are arranged side by side, there by making up the direction indication guide unit 13 long in the lateral direction and the lighting position of the direction indication guide unit 13 is changed based on the distance information provided by the distance measurement sensor 9, whereby it is made possible to guide the direction in which the subject K is directed (angle) into the optimum position.

According to the invention, an iris image pickup failure is previously circumvented and an iris image is acquired, so that an iris image for iris authentication can be acquired efficiently and the processing time to authentication processing can be shortened.

What is claimed is:

1. An iris image pickup apparatus comprising:
   an image pickup unit for picking up an iris image of a subject in a first or second position;
   a direction indication guide unit for indicating to the subject that the subject will be guided to a second position and guiding the subject in a direction from the first position to the second position if the iris image picked up at the first position is not suited for authentication; and
   a guide unit that emits light to guide a direction of the subject,
   wherein the second position is at a position with respect to the image pickup unit different from that of the first position,
   wherein said image pickup unit includes an optical axis directed toward the subject, and
   wherein said optical axis is arranged between said guide unit and said direction indication guide unit.

2. The iris image pickup apparatus of claim 1,
   wherein said direction indication guide unit is configured to inform the subject of the iris image pickup timing of the iris image to be picked up at the first position before said iris image is picked up at the first position.

3. The iris image pickup apparatus as claimed in claim 2 further comprising an iris illumination unit for applying illumination light in the direction of the subject, wherein an angle of the illumination light reflected off the subject increases as the subject is guided from the first position to the second position.

4. The iris image pickup apparatus as claimed in claim 2, wherein said direction indication guide unit includes a light emitting diode, and the subject is informed of the iris image pickup timing according to the lighting pattern of the light emitting diode.

5. The iris image pickup apparatus as claimed in claim 2, wherein said direction indication guide unit informs the subject of the iris image pickup timing more than once.

6. The iris image pickup apparatus as claimed in claim 2, further comprising a flash unit for applying light for forcibly inducing the subject to blink.

7. The iris image pickup apparatus as claimed in claim 2, wherein an additional iris image is picked up before the subject is informed of the iris image pickup timing.

8. The iris image pickup apparatus of claim 1, wherein said image pickup unit is a second image pickup unit which picks up the iris image by a telephoto lens, the apparatus further comprising:
   a first image pickup unit for picking up an image of a subject by a wide-angle lens;
   wherein the direction indication guide unit displays a guide indication for indicating to the subject that the subject will be redirected to the second position and for redirecting the subject's face from the first position to the second position before said second image pickup unit picks up the iris image when it is determined that the subject wears glasses from image pickup information of said first image pickup unit,
   wherein said direction indication guide unit is configured to inform the subject of the iris image pickup timing of said iris image before said iris image is picked up.

9. The iris image pickup apparatus as claimed in claim 8, wherein said direction indication guide unit includes a light emitting diode, and the subject is informed of the iris image pickup timing according to the lighting pattern of the light emitting diode.

10. The iris image pickup apparatus as claimed in claim 8, wherein said direction indication guide unit informs the subject of the iris image pickup timing more than once.

11. The iris image pickup apparatus as claimed in claim 8, further comprising a flash unit for applying light for forcibly inducing the subject to blink.

12. The iris image pickup apparatus as claimed in claim 8, wherein an additional iris image is picked up before the subject is informed of the iris image pickup timing.

13. The iris image pickup apparatus of claim 1, wherein said image pickup unit is a second image pickup unit which picks up the iris image by a telephoto lens, the apparatus further comprising:
    a first image pickup unit for picking up an image of a subject by a wide-angle lens;
    an iris illumination unit for applying illumination light in an iris direction of the subject; and
    a control unit for operating said direction indication guide unit for redirecting and guiding the subject in a direction from the first position to the second position before said second image pickup unit picks up an iris image when it is determined that the subject wears glasses from image pickup information of said first image pickup unit,
    wherein said first image pickup unit and said second image pickup unit are placed between said direction indication guide unit and said iris illumination unit, and,
    wherein the second position is at a position with respect to the second image pickup unit different from that of the first position, and
    wherein said direction indication guide unit is configured to inform the subject of the iris image pickup timing of said iris image before said iris image is picked up.

14. The iris image pickup apparatus as claimed in claim 13, wherein said direction indication guide unit includes a light emitting diode, and the subject is informed of the iris image pickup timing according to the lighting pattern of the light emitting diode.

15. The iris image pickup apparatus as claimed in claim 13, wherein said direction indication guide unit informs the subject of the iris image pickup timing more than once.

16. The iris image pickup apparatus as claimed in claim 13, further comprising a flash unit for applying light for forcibly inducing the subject to blink.

17. The iris image pickup apparatus as claimed in claim 13, wherein an additional iris image is picked up before the subject is informed of the iris image pickup timing.

18. An iris image pickup apparatus comprising:
    an image pickup unit for picking up an iris image of a subject in a first or second position;
    a direction indication guide unit for indicating to the subject that the subject will be guided to a second position and guiding the subject in a direction from the first position to the second position if the iris image picked up at the first position is not suited for authentication; and
    a detection unit for detecting the distance to the subject,
    wherein the second position is at a position with respect to the image pickup unit different from that of the first position, and wherein a guide display position of said direction indication guide unit determines the angle in which the subject is to be directed based on detection information provided by the detection unit.

19. An iris image pickup apparatus comprising:
a first image pickup unit for picking up an image of a subject by a wide-angle lens;
a second image pickup unit for picking up an iris image of the subject in a first or second position by a telephoto lens;
a direction indication guide unit for displaying guide indication for indicating to the subject that the subject will be redirected to the second position and for redirecting the subject's face from the first position to the second position before said second image pickup unit picks up an iris image when it is determined that the subject wears glasses from image pickup information of said first image pickup unit; and
a detection unit for detecting the distance to the subject,
wherein the second position is at a position with respect to the second image pickup unit different from that of the first position, and
wherein a guide display position of said direction indication guide unit determines an angle in which the subject is to be redirected based on detection information provided by the detection unit.

20. An iris image pickup apparatus comprising:
a first image pickup unit for picking up an image of a subject by a wide-angle lens;
a second image pickup unit for picking up an iris image of the subject in a first or second position by a telephoto lens;
a direction indication guide unit for indicating to the subject that the subject will be redirected to the second position and for indicating the direction in which the subject is redirected;
an iris illumination unit for applying illumination light in an iris direction of the subject;
a control unit for operating said direction indication guide unit for redirecting and guiding the subject in a direction from the first position to the second position before said second image pickup unit picks up an iris image when it is determined that the subject wears glasses from image pickup information of said first image pickup unit; and
a detection unit for detecting the distance to the subject,
wherein said first image pickup unit and said second image pickup unit are placed between said direction indication guide unit and said iris illumination unit,
wherein the second position is at a position with respect to the second image pickup unit different from that of the first position, and
wherein a guide display position of said direction indication guide unit determines an angle in which the subject is to be redirected based on detection information provided by the detection unit.

* * * * *